[19] United States Patent
Baldwin et al.

[11] Patent Number: 4,539,317
[45] Date of Patent: Sep. 3, 1985

[54] 4-SUBSTITUTED AMINO-3-[3-ALKYLINDOLOAMINO-2-HYDROXYPROPOXY] THIADIAZOLES, COMPOSITIONS AND PHARMACEUTICAL USE

[75] Inventors: John J. Baldwin, Gwynedd Valley; Gerald S. Ponticello, Lansdale, both of Pa.

[73] Assignee: Merck & Co., Inc., Rahway, N.J.

[21] Appl. No.: 597,990

[22] Filed: Apr. 9, 1984

[51] Int. Cl.$^3$ ............... A61K 31/425; A61K 31/535; C07D 417/12; C07D 417/14
[52] U.S. Cl. .................................... 514/222; 514/229; 514/252; 514/362; 544/58.7; 544/62; 544/134; 544/367; 548/135
[58] Field of Search .............. 544/58.7, 62, 134, 367; 548/135; 424/246, 248.51, 250, 270

[56] References Cited

U.S. PATENT DOCUMENTS

| | | | |
|---|---|---|---|
| 3,729,469 | 4/1973 | Wasson | 548/135 |
| 4,134,983 | 1/1979 | Baldwin | 424/267 |
| 4,440,774 | 4/1984 | Baldwin | 424/267 |

*Primary Examiner*—Robert W. Ramsuer
*Attorney, Agent, or Firm*—Alice O. Robertson; Salvatore C. Mitri

[57] ABSTRACT

Novel 4-substituted amino-3-[3-alkylindoloamino-2-hydroxypropoxy] thiadiazole compounds and methods for their preparation are disclosed. These compounds and their salts exhibit pharmacological activity including antihypertensive and β-adrenergic blocking activity.

8 Claims, No Drawings

4-SUBSTITUTED AMINO-3-[3-ALKYLINDOLOAMINO-2-HYDROXYPROPOXY] THIADIAZOLES, COMPOSITIONS AND PHARMACEUTICAL USE

BACKGROUND OF THE INVENTION

The present invention is directed to novel 4-substituted amino-3-[3-alkylindoloamino-2-hydroxypropoxy]thiadiazole compounds which have antihypertensive and β-adrenergic blocking activity.

Various chemical agents are available for treating hypertension in man and animals. One class of agents, known as β-adrenergic blocking agents, affect cardiac, vascular and pulmonary functions and can be mild antihypertensives. Specifically, these agents have the capability of reducing heart rate, counteracting vasodepression and suppressing bronchodilation. β-adrenergic blocking agents, their chemical structure and activity, are disclosed in "Clinical Pharmacology and Therapeutics" 10, 292–306 (1969). Various β-adrenergic blocking agents are also described in the following patents: U.S. Pat. No. 3,048,387; U.S. Pat. No. 3,337,628; U.S. Pat. No. 3,655,663; U.S. Pat. No. 3,794,650; U.S. Pat. No. 3,832,470; U.S. Pat. No. 3,836,666; U.S. Pat. No. 3,850,945; U.S. Pat. No. 3,850,946; U.S. Pat. No. 3,850,947; U.S. Pat. No. 3,852,291; U.S. Pat. No. 4,143,983; U.S. Pat. No. 4,199,580; and British No. 1,194,548.

W. E. Kreighbaum et al. [*J. Med. Chem.*, 23, 285–289 (1980)] disclose aryloxypropanolamine compounds, some of which exhibit antihypertensive activity by the combination of β-adrenergic receptor antagonist activity with vasodilating action.

Where an antihypertensive agent acts principally via vasodilation, it may cause undesirable side effects such as substantially increased heart rate (tachycardia). This undesirable side effect can be modified by the presence of β-adrenergic blockade in the molecule.

SUMMARY OF THE INVENTION

Novel 4-substituted amino-3-[3-alkylindoloamino-2-hydroxypropoxy]thiadiazoles have been discovered which exhibit antihypertensive and β-adrenergic blocking activity.

DESCRIPTION OF PREFERRED EMBODIMENTS

The compounds of the present invention have the general formula:

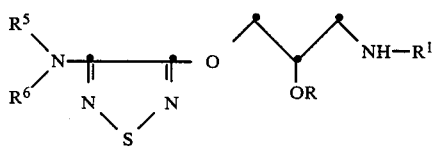

I wherein:
R is hydrogen,

wherein $R_a$ is $C_1$–$C_8$ alkyl; $C_6$ or $C_{10}$ aryl;
$R^1$ is

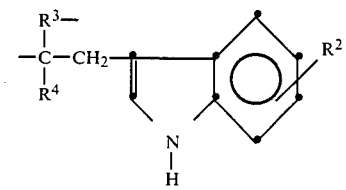

wherein:
$R^2$ is
  hydrogen;
  halo (F, Br, Cl);
  hydroxy;
  $C_1$–$C_8$ alkyl;
  $C_1$–$C_8$ alkoxy;
$R^3$ and $R^4$ are independently hydrogen; $C_1$–$C_5$ alkyl;
$R^5$ and $R^6$ are independently
  lower alkyl of $C_1$–$C_6$;
  or $R^5$ and $R^6$, together with the N atom, can be joined to form a 5- or 6-membered ring wherein the 6-membered ring can contain an O, S, N—H, or N-lower ($C_1$–$C_6$) alkyl heteroatom; and,
the pharmacologically acceptable acid addition salts thereof.

Preferred are those compounds of Formula I wherein:
R is hydrogen,
$R^1$ is

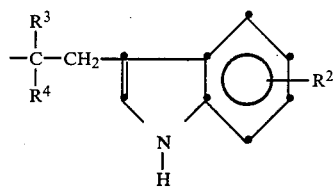

wherein:
$R^2$ is
  hydrogen;
  halo;
  hydroxy;
  $C_1$–$C_8$ alkoxy;
$R^3$ and $R^4$ are independently hydrogen; $C_1$–$C_5$ alkyl; and,
$R^5$ and $R^6$ together with the N atom, form a 6-membered heterocyclic ring containing an O, S, or N-lower ($C_1$–$C_6$) alkyl heteroatom.

More preferred are those compounds of Formula I wherein:
R is hydrogen;
$R^1$ is

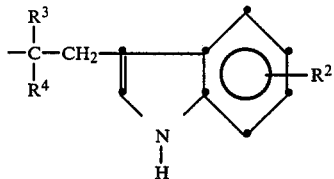

wherein:
$R^2$ is hydrogen;
$R^3$ and $R^4$ are independently hydrogen; or methyl; and, $R^5$ and $R^6$ together with the N atom, form a 6-membered heterocyclic ring containing an O or S heteroatom.

The compounds of the present invention include the N-oxides and the non-toxic pharmacologically acceptable acid addition salts thereof. The acid addition salts are prepared by treating the compounds of the invention with an appropriate amount of a suitable organic or inorganic acid. Examples of useful organic acids are carboxylic acids such as maleic acid, tartaric acid, acetic acid, pamoic acid, oxalic acid, propionic acid, salicylic acid, succinic acid, citric acid, malic acid, isethionic acid, and the like; useful inorganic acids are hydrohalo acids such as HCl, HBr and HI, sulfuric acid, $H_3PO_4$, and the like.

The compounds of the present invention include all of their optical isomer forms. In other words, the compounds include mixtures containing the optical isomers such as racemic mixtures, as well as the individual optical isomers.

The compounds of the present invention are active (1) as antihypertensives; i.e., they exhibit blood pressure lowering effect in hypertensive animals, and (2) as $\beta$-adrenergic blocking agents.

The antihypertensive effect of the compounds of the invention was determined by administering them (orally or intraperitoneally) to spontaneously hypertensive (SH) rats and measuring the effect on their blood pressure and heart rate. The compounds of the invention, generally administered as a salt; e.g., the hydrochloride, were found to lower the SH rats' blood pressure and heart rate.

The $\beta$-adrenergic blocking activity ($\beta$-blockade) the present compounds was determined by measuring their ability to block isoproterenol induced tachycardia, vasodepression and bronchodilatation in animals. Intravenous administration of the compounds, (generally as acid addition salts) was used for this evaluation and they exhibited their ability to effect $\beta$-blockade in addition to having the aforesaid antihypertensive effect.

The ability of the compounds of the present invention to reduce blood pressure in the SH rat indicates that these compounds and their salts may be useful to treat essential hypertension in humans and may also be useful in modifying undesirable increase in heart rate (tachycardia) by their presence in the molecule.

The $\beta$-adrenergic blocking effectiveness of the compounds of the present invention indicates that they are also useful to treat humans suffering from undesirable conditions such as angina pectoris or certain arrhythmias which are known to be amenable to treatment with $\beta$-adrenergic blocking agents.

For use as antihypertensives and/or $\beta$-adrenergic blocking agents, the present compounds can be administered orally, parenterally or transdermally; i.e., intravenously, interperitoneally, topically, etc., and in any suitable dosage form. The compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral adminstration; e.g., dissolved or dispersed in a suitable liquid carrier or emulsifed, or (c) transdermally. The ratio of active compound to compounding ingredients; i.e., carrier, diluent, etc., will vary as the dosage form requires. Whatever dosage form is used, the amount of the compound of the present invention administered should be sufficient to effect (a) a reduction in blood pressure of a patient suffering from hypertension and/or (b) desirable level of $\beta$-blockade in a patient. Generally, doses of the present compounds of from about 0.01 to about 50 mg/kg and preferably from about 0.1 to about 20 mg/kg of body weight per day may be used. Dosage may be single or multiple depending on the daily total required and the unit dosage.

Following are examples illustrating representative pharmaceutical formulations containing the compounds of the present invention. Conventional techniques are used to prepare these formulations.

| INGREDIENT | AMOUNT (Mg.) |
|---|---|
| TABLET FORMULATION I | |
| 3-{2-hydroxy-3-[2-(3-indolyl)-1,1-dimethylethylamino]propoxy}-4-(N—morpholino)-1,2,5-thiadiazole | 40.0 |
| calcium phosphate | 120.0 |
| lactose | 50.0 |
| starch | 23.5 |
| magnesium stearate | 1.5 |
| OCULAR FORMULATION | |
| 3-{2-hydroxy-3-[2-(3-indolyl)-1,1-dimethylethylamino]propoxy}-4-(N—morpholino)-1,2,5-thiadiazole | 15.0 |
| sodium phosphate monobasic .2H$_2$O | 6.10 |
| dibasic sodium phosphate .12H$_2$O | 16.80 |
| benzalkonium chloride | 0.10 |
| sodium hydroxide q.s. | pH 6.8 |
| water for injection q.s. | 1.0 ml |
| LIQUID SUSPENSION | |
| 3-{2-hydroxy-3-[2-(3-indolyl)-1,1-dimethylethylamino]propoxy}-4-(N—morpholino)-1,2,5-thiadiazole | 5.0 |
| Veegum H.V. | 3.0 |
| methyl paraben | 1.0 |
| kaolin | 10.0 |
| glycerin | 250.0 |
| water, q.s. | 1 liter |
| CAPSULE FORMULATION | |
| 3-{2-hydroxy-3-[2-(3-indolyl)-1,1-dimethylethylamino]propoxy}-4-(N—morpholino)-1,2,5-thiadiazole | 5.0 |
|  | 250 |
| lactose, U.S.P. | 93 |
| talc | 7 |
| INJECTABLE SOLUTION | |
| 3-{2-hydroxy-3-[2-(3-indolyl)-1,1-dimethylethylamino]propoxy}-4-(N—morpholino)-1,2,5-thiadiazole | 5.0 |
|  | 5 |
| sodium chloride | 9 |
| distilled water, q.s. 1.0 ml. | |

The compounds of the present invention can be prepared by any convenient method. One such method is shown in the following Reaction Scheme wherein the R–R$^6$ groups are as defined above, unless otherwise indicated. Also, unless otherwise indicated, the starting materials employed are those which are known in the literature, are commercially available, or can be prepared by methods known to those skilled in the art.

REACTION SCHEME

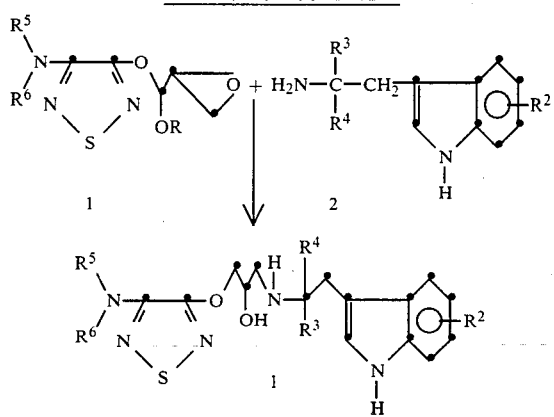

As shown in the foregoing Reaction Scheme, epoxide 1 is reacted with amine 2 in a suitable solvent such as isopropanol, methanol, ethanol, CH$_2$Cl$_2$, tetrahydrofuran (THF), ether (Et$_2$O), toluene, and the like, at a temperature of about 0° to the reflux temperature of the solvent for about 1–48 hours, preferably in isopropanol at 70° for 24 hours, to yield a compound I of the invention. Compound 2 can be prepared as described by W. E. Krieghbaum et al. [*J. Med. Chem.*, 23,285 (1980)].

The following example is set forth to illustrate the preparation of a representative compound of the present invention and should not be construed as being limitative of the scope of the compounds of the invention. Unless otherwise indicated, all parts and percentages are by weight, all temperatures are in degrees Celsius, and all analyses were computed to within 0.4%.

EXAMPLE 1

3-{2-Hydroxy-3-[2-(3-indolyl)-1,1-dimethylethylamino]propoxy}-4-(N-morpholino)-1,2,5-thiadiazole (5)

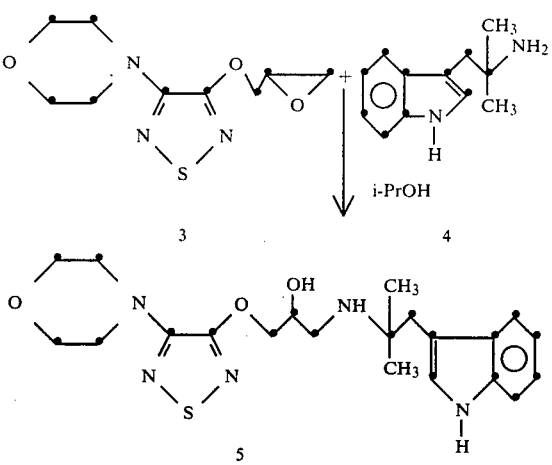

A mixture of 3-(2,3-epoxy-1-propoxy)-4-morpholino-1,2,5-thiadiazole 3 (1.50 g, 0.0062 m) and α,α-dimethyl-1H-indole-3-ethanamine 4 (1.39 g, 0.0074 m) in isopropanol (35 ml) was stirred at 70° C. for 21 hours. The solvent was evaporated under reduced pressure and the residue chromatographed on silica gel, eluting with 10% MeOH—CHCl$_3$ saturated with NH$_3$, to yield 5 (2.14 g, 80%). An analytical sample melted at 113°–115° C. after recrystallization from acetonitrile.

Anal. Calcd. for C$_{21}$H$_{29}$N$_5$O$_3$S: C, 58.44; H, 6.77; N, 16.23. Found: C, 58.72 and 58.62; H, 6.95 and 7.03; N, 16.53 and 16.37.

Following the procedures and methods described in The Reaction Scheme and the Example, additional compounds of the invention can be prepared as shown in Table I below.

TABLE I

Additional Compounds of Formula I

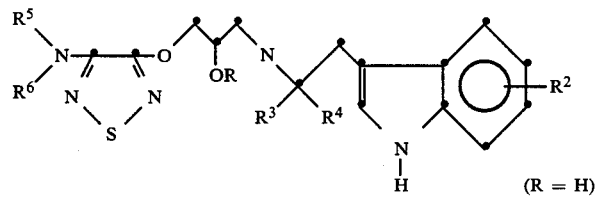

| | R | R$^2$ | R$^3$ | R$^4$ | R$^5$ | R$^6$ |
|---|---|---|---|---|---|---|
| (a) | H | 2-CH$_3$ | CH$_3$ | H | CH$_3$ | CH$_3$ |
| (b) | " | 1-CH$_3$ | H | " | CH$_2$CH$_3$ | CH$_2$CH$_3$ |
| (c) | " | 5-Br | CH$_3$CH$_2$ | " | CH$_2$CH$_2$OH | CH$_2$CH$_2$OH |
| (d) | O<br>‖<br>—C—CH$_3$ | 5-CH$_3$O | CH$_3$CH$_2$CHCH | " | CH$_2$CH$_2$OCH$_3$ | CH$_2$CH$_2$OCH$_3$ |
| (e) | O<br>‖<br>—C—C$_6$H$_5$ | 2-CH$_3$ | CH$_3$ | CH$_3$ | CH$_2$CH$_2$OH | CH$_2$CH$_2$OH |

TABLE I-continued
Additional Compounds of Formula I

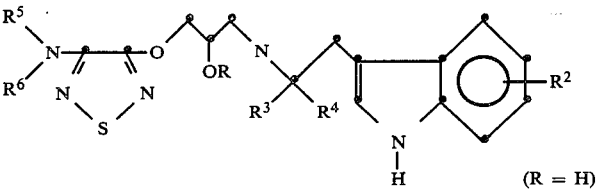
(R = H)

| | R | R² | R³ | R⁴ | R⁵ | R⁶ |
|---|---|---|---|---|---|---|
| (f) | H | 5-CH₃O | CH₃ | CH₃ | CH₂—CH₂ | CH₂—CH₂ (N-CH₃) |
| (g) | " | 5-Br | CH₃ | CH₃ | CH₂—CH₂ | CH₂—CH₂ (O) |
| (h) | $-\overset{O}{\underset{\|}{C}}-C_6H_5$ | 2-CH₃ | CH₃ | CH₃ | CH₂—CH₂ | CH₂—CH₂ (S) |
| (i) | $-\overset{O}{\underset{\|}{C}}-CH_3$ | 2-CH₃ | CH₃ | CH₃ | CH₂—CH₂—CH₂—CH₂ | |

What is claimed is:

1. A compound having the formula:

wherein:
R is hydrogen;

$$-\overset{O}{\underset{\|}{C}}R_a$$

wherein $R_a$ is $C_1$–$C_8$ alkyl; $C_6$ or $C_{10}$ aryl;
$R^1$ is

wherein:
$R^2$ is
   hydrogen;
   halo (F, Br, Cl);
   hydroxy;
   $C_1$–$C_8$ alkyl;
   $C_1$–$C_8$ alkoxy;

$R^3$ and $R^4$ are independently hydrogen; $C_1$–$C_5$ alkyl;
$R^5$ and $R^6$ are independently
   lower alkyl of $C_1$–$C_6$;
   or $R^5$ and $R^6$, together with the N atom, can be joined to form a 5- or 6-membered ring wherein the 6-membered ring can contain an O, S, N—H, or N-lower ($C_1$–$C_6$) alkyl heteroatom; and,
the pharmacologically acceptable acid addition salts thereof.

2. A compound of claim 1 wherein:
R is hydrogen;
$R^1$ is

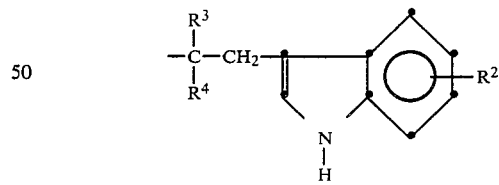

wherein:
$R^2$ is
   hydrogen;
   halo;
   hydroxy;
   $C_1$–$C_8$ alkoxy;
$R^3$ and $R^4$ are independently hydrogen; $C_1$–$C_{15}$ alkyl; and,
$R^5$ and $R^6$ together with the N atom, form a 6-membered heterocyclic ring containing an O, S, or N-lower ($C_1$–$C_6$) alkyl heteroatom.

3. A compound of claim 2 wherein; R is hydrogen;
$R^1$ is

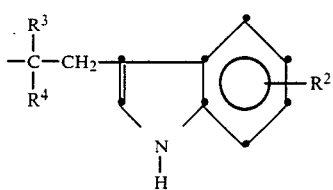

wherein

R² is hydrogen;

R³ and R⁴ are independently hydrogen; or methyl; and,

R⁵ and R⁶, together with the N atom, form a 6-membered heterocyclic ring containing an O or S heteratom.

4. A compound having the formula:

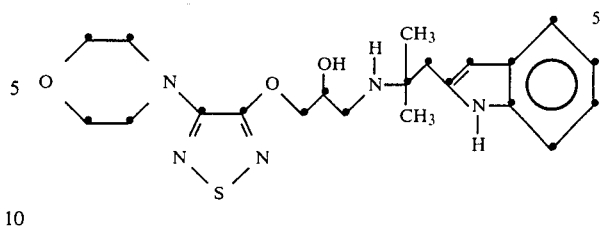

5. The compound of claim 4 which is in the R configuration.

6. The compound of claim 4 which is in the S configuration.

7. A pharmaceutical composition useful for treating hypertension or effecting β-adrenergic blockade comprising a pharmaceutically acceptable carrier; and, an antihypertensively or β-adrenergic blockading effective amount of a compound of claim 1.

8. A method for treating hypertension or effecting β-adrenergic blockade comprising administering to a patient in need of such treatment an antihypertensively or β-adrenergic blockading effective amount of a compound of claim 1.

* * * * *